United States Patent
Gu et al.

(10) Patent No.: US 9,642,597 B2
(45) Date of Patent: May 9, 2017

(54) ULTRASONIC DIAGNOSTIC INSTRUMENT AND MANUFACTURING METHOD THEREOF

(71) Applicant: SAMSUNG MEDISON CO., LTD., Gangwon-do (KR)

(72) Inventors: Jin Ho Gu, Seongnam-si (KR); Won Hee Lee, Seoul (KR); Jae-Yk Kim, Seongnam-si (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 246 days.

(21) Appl. No.: 14/537,717

(22) Filed: Nov. 10, 2014

(65) Prior Publication Data
US 2015/0157292 A1    Jun. 11, 2015

(30) Foreign Application Priority Data
Dec. 9, 2013    (KR) .......................... 10-2013-0152167

(51) Int. Cl.
*A61B 8/00*    (2006.01)
*G10K 11/02*    (2006.01)

(52) U.S. Cl.
CPC .......... *A61B 8/4444* (2013.01); *A61B 8/4488* (2013.01); *A61B 8/54* (2013.01); *G10K 11/02* (2013.01); *Y10T 29/49005* (2015.01)

(58) Field of Classification Search
CPC ....... A61B 8/4444; A61B 8/4488; A61B 8/54; G10K 11/02; Y10T 29/49005
See application file for complete search history.

(56) References Cited

U.S. PATENT DOCUMENTS

| | | |
|---|---|---|
| 2005/0275313 A1 | 12/2005 | Yamashita et al. |
| 2011/0114303 A1* | 5/2011 | Rhim ....................... A61B 8/00 165/185 |
| 2013/0315035 A1 | 11/2013 | Tai |

FOREIGN PATENT DOCUMENTS

| | | |
|---|---|---|
| EP | 0727259 A2 | 8/1996 |
| JP | 2007-282743 A | 11/2007 |
| JP | 2010-214116 A | 9/2010 |

(Continued)

OTHER PUBLICATIONS

Korean Notice of Patent Allowance dated Jan. 18, 2016 in Korean Patent Application No. 10-2013-0152167 (partial English Translation).

(Continued)

*Primary Examiner* — Michael Rozanski
(74) *Attorney, Agent, or Firm* — McDermott Will & Emery LLP

(57) ABSTRACT

Disclosed are an ultrasonic diagnostic instrument and a manufacturing method thereof. The ultrasonic diagnostic instrument includes a matching layer, at least one transducer provided at a lower surface of the matching layer to generate ultrasonic waves, a first acoustic absorption layer provided at a lower surface of the transducer to transmit an ultrasonic wave generation signal to the transducer, a controller provided at a lower surface of the first acoustic absorption layer to control operation of the transducer, the controller having a recess formed in a lower surface thereof, and a second acoustic absorption layer provided at a lower surface of the controller and having an insert formed at an upper surface thereof, the insert corresponding to the recess of the controller.

16 Claims, 11 Drawing Sheets

(56) References Cited

FOREIGN PATENT DOCUMENTS

| KR | 20100010358 A | 2/2010 |
| KR | 20120005975 A | 1/2012 |
| WO | 2010/011034 A1 | 1/2010 |

OTHER PUBLICATIONS

Extended European Search Report dated Sep. 8, 2015 issued in European Patent Application No. 14185778.9.

* cited by examiner

ULTRASONIC DIAGNOSTIC INSTRUMENT AND MANUFACTURING METHOD THEREOF

CROSS-REFERENCE TO RELATED APPLICATION

This application claims the benefit of Korean Patent Applications No. 2013-0152167, filed on Dec. 9, 2013 in the Korean Intellectual Property Office, the disclosure of which is incorporated herein by reference.

BACKGROUND

1. Field

Embodiments of the present invention relate to an ultrasonic diagnostic instrument, which achieves enhanced heat dissipation efficiency via an increased surface area of a radiator and also achieves increased durability with a packaging structure thereof, and a method of manufacturing the ultrasonic diagnostic instrument.

2. Description of the Related Art

An ultrasonic diagnostic instrument is a device that transmits an ultrasonic signal from the body surface of a subject to an internal body region, and acquires tomography of soft tissues or blood flow in a non-invasive manner using information regarding the reflected ultrasonic signal (ultrasound echo signal). As compared to other diagnostic imaging apparatuses, such as an X-ray diagnostic apparatus, X-ray Computerized Tomography (CT) scanner, Magnetic Resonance Imaging (MRI) apparatus, nuclear medicine diagnostic apparatus, etc., the ultrasonic diagnostic instrument is small and cheap, enables real-time image display, and exhibits high safety due to less X-ray exposure. Owing to these advantages, the ultrasonic diagnostic instrument has been widely used for diagnosis of heart, abdomen, urinary, and ob-gyn diseases.

A typical ultrasonic diagnostic instrument, to acquire an ultrasonic image of a subject, includes a transducer to transmit an ultrasonic signal to the subject and to receive an ultrasound echo signal reflected from the subject.

More specifically, the ultrasonic diagnostic instrument may include a transducer to implement inter-conversion between an electrical signal and an acoustic signal via vibration of a piezoelectric material, a matching layer to reduce a difference in acoustic impedances between the transducer and the subject to allow ultrasonic waves generated in the transducer to be transmitted to the subject to the maximum extent, a lens layer to collimate the ultrasonic waves moving forward of the transducer on a specific point, and an acoustic absorption layer to prevent the ultrasonic waves from moving rearward of the transducer to prevent image distortion.

Recently, smaller size and higher performance of the transducer included in the ultrasonic diagnostic instrument causes generation of heat, and therefore research into heat transfer to prevent heat from being transferred forward of the ultrasonic diagnostic instrument or research into cooling of the ultrasonic diagnostic instrument has been conducted.

SUMMARY

It is an aspect of the present invention to provide an ultrasonic diagnostic instrument having a packaging structure in which inserts are formed at a lower surface of a controller and recesses are formed at an upper surface of a second acoustic absorption layer, the recesses corresponding to the inserts of the controller, and a method of manufacturing the ultrasonic diagnostic instrument.

Additional aspects of the invention will be set forth in part in the description which follows and, in part, will be obvious from the description, or may be learned by practice of the invention.

In accordance with one embodiment, an ultrasonic diagnostic instrument includes a matching layer, at least one transducer provided at a lower surface of the matching layer to generate ultrasonic waves, a first acoustic absorption layer provided at a lower surface of the transducer to transmit an ultrasonic wave generation signal to the transducer, a controller provided at a lower surface of the first acoustic absorption layer to control operation of the transducer, the controller having a recess formed in a lower surface thereof, and a second acoustic absorption layer provided at a lower surface of the controller and having an insert formed at an upper surface thereof, the insert corresponding to the recess of the controller.

The insert may have one shape among cylindrical, semi-spherical, tetrahedral, pentagonal, and hexahedral shapes.

The at least one transducer may include a plurality of transducers in the form of a matrix array, a linear array, a convex array, or a concave array.

The controller may include a plurality of semiconductor elements to control the respective transducers, and the semiconductor elements take the form of a matrix array, a linear array, a convex array, or a concave array.

A width of each semiconductor element may be equal to or greater than a width of a corresponding one of the transducers controlled by the semiconductor element, and may be equal to or less than the sum of a width of a corresponding one of the transducers controlled by the semiconductor element and a gap between the corresponding transducer and another transducer located at one side thereof.

A thickness of each semiconductor element may have a value acquired by dividing the wavelength of ultrasonic waves generated by a corresponding one of the transducers controlled by the semiconductor element by an even number.

In accordance with another embodiment, a method of manufacturing an ultrasonic diagnostic instrument, includes providing a matching layer, providing at least one transducer at a lower surface of the matching layer, providing a first acoustic absorption layer at a lower surface of the transducer, forming a recess in a lower surface of a controller, providing the controller at a lower surface of the first acoustic absorption layer, forming an insert at an upper surface of a second acoustic absorption layer, the insert corresponding to the recess of the controller, and providing the second acoustic absorption layer at the lower surface of the controller.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
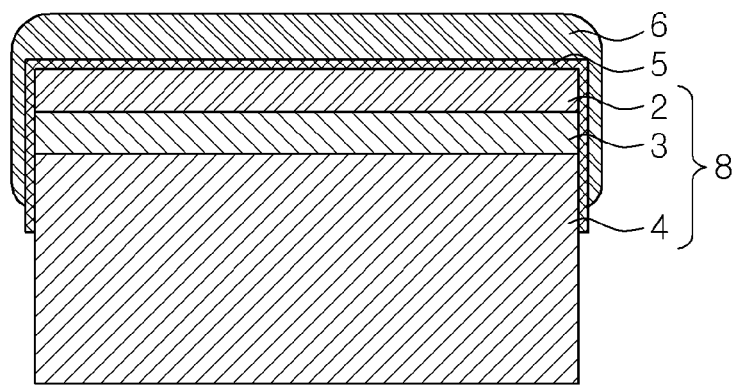
FIG. 1 is a sectional view of an acoustic module in an ultrasonic diagnostic instrument according to one embodiment.

Reference will now be made in detail to the embodiments of the present invention, examples of which are illustrated in the accompanying drawings, to allow those skilled in the art to easily understand and reproduce the embodiments of the present invention. In the following description of the embodiments of the present invention, a detailed description of known functions or configurations incorporated herein will be omitted when it may make the subject matter of the disclosure rather unclear.

The terms used in the following description are selected by taking into consideration the functions obtained in accordance with the embodiments, and these terms may be replaced by other terms based on intensions of those skilled in the art, customs, or the like. Hence, the meanings of terms used in the following description of the embodiments must follow definitions concretely described in the specification, and must be construed as having a general meaning typically recognized by those skilled in the art so long as there are no concrete definitions.

In addition, even if selectively described aspects of the present specification or selectively described configurations of the embodiments are shown as a single integrated configuration in the drawings, so long as there is no additional explanation, it should be understood that they may be freely combined with one another if those skilled in the art judge that the combinations have no clear technical contradictions.

Hereinafter, one embodiment of an ultrasonic diagnostic instrument 1 will be described with reference to the accompanying drawings.

FIG. 1 is a sectional view of an acoustic module 8 in the ultrasonic diagnostic instrument 1 according to one embodiment.

As exemplarily shown in FIG. 1, the ultrasonic diagnostic instrument 1 may include an acoustic module 8 composed of a transducer 3, an acoustic absorption layer 4 disposed at a lower surface of the transducer 3, and a matching layer 2 disposed at an upper surface of the transducer 3, a protective layer 5 covering an upper surface and a portion of a side surface of the acoustic module 8, and a lens layer 6 covering an upper surface and a side surface of the protective layer 5.

Examples of ultrasonic transducers may include a magnetostrictive ultrasonic transducer using magnetostrictive effects of a magnetic material, a capacitive micromachined ultrasonic transducer to transmit and receive ultrasonic waves using vibration of several hundred or thousand micromachined thin films, and a piezoelectric ultrasonic transducer using piezoelectric effects of a piezoelectric material. Hereinafter, a piezoelectric ultrasonic transducer will be described as one embodiment of the transducer.

Piezoelectric effects or inverse piezoelectric effects are effects in which voltage is generated when mechanical pressure is applied to a material, and mechanical deformation occurs upon voltage application. A material having the effects may be referred to as a piezoelectric material. That is, a piezoelectric material may convert electrical energy into mechanical vibration energy or vice versa.

The transducer 3 may be formed of a piezoelectric material. Thus, when an electrical signal is applied to the ultrasonic diagnostic instrument 1, the transducer 3 may convert the electrical signal into mechanical vibration, thereby generating ultrasonic waves.

The piezoelectric material constituting the transducer 3 may include lead zirconate titanate (PZT) ceramics, PZMT single-crystals made of magnesium niobate and lead zirconate titanate solid solution, or PZNT single-crystals made of zinc-niobate and lead zirconate titanate solid solution. Naturally, various other materials to convert an electrical signal into mechanical vibration may be used as one example of the piezoelectric material constituting the transducer 3.

In addition, the transducer 3 may be arranged in a single-layer or in a stack of multiple layers. Generally, the transducer 3 in the form of a stack may be more advantageous in terms of impedance and voltage adjustment, thus achieving high energy conversion efficiency and tender spectrums. Naturally, various other structures in consideration of the performance of the transducer 3 may be used as one example of the structure of the transducer 3.

The acoustic absorption layer 4 may be installed to the lower surface of the transducer 3 to absorb ultrasonic waves generated in and moving rearward of the transducer 3, thereby preventing ultrasonic waves from moving rearward of the transducer 3. Consequently, the acoustic absorption layer 4 may prevent image distortion. The acoustic absorption layer 4 may be formed in multiple layers to increase attenuation or prevention of ultrasonic waves. Naturally, various structures to increase attenuation or prevention of ultrasonic waves may be used as one example of the structure of the acoustic absorption layer 4.

The matching layer 2 may be installed at the upper surface of the transducer 3. The matching layer 2 may reduce a difference in acoustic impedances between the transducer 3 and a subject to match the acoustic impedances of the transducer 3 and the subject with each other, thereby allowing ultrasonic waves generated in the transducer 3 to be efficiently transmitted to the subject. To this end, the impedance of the matching layer 2 may have a median value between the acoustic impedance of the transducer 3 and the acoustic impedance of the subject.

The matching layer 2 may be formed of glass or a resin. Naturally, various other materials to match the acoustic impedances of the transducer 3 and the subject with each other may be used as one example of a constituent material of the matching layer 2.

In addition, the matching layer 2 may include a plurality of matching layers 2 to ensure stepwise variation of acoustic impedance from the transducer 3 to the subject, and the matching layers 2 may be formed of different materials. Naturally, various other structures to ensure stepwise variation of acoustic impedance may be used as one example of the structure of the matching layer 2.

The transducer 3 and the matching layer 2 may be processed into a 2-dimensional (2D) matrix array by dicing, or may be processed into a 1D matrix array.

The protective layer 5 may be installed to cover an upper surface of the matching layer 2 and a portion of the side surface of the acoustic module 8. The protective layer 5 may include a chemical shield to protect internal elements from water and medicines used for disinfection. The chemical shield may be formed by coating or depositing a conductive material on a surface of a moisture-proof and chemical-resistant film. For example, the chemical shield may be formed by implementing Parylene coating of a polymer film on the upper surface of the matching layer 2 and a portion of the side surface of the acoustic module 8. In another example, the chemical shield may be formed by sputtering on a surface of a polymer film.

In addition, the protective layer 5 may include a Radio Frequency (RF) shield to prevent leakage of RF waves from the transducer 3 as well as introduction of an external RF signal. Naturally, various other configurations to prevent introduction/leakage of RF components may be used as one example of a constituent configuration of the protective layer 5.

The lens layer 6 may be installed to cover the upper surface and the side surface of the protective layer 5. The lens layer 6 may be formed of a low-attenuation material to prevent attenuation of an ultrasonic signal generated in the transducer 3. For example, the lens layer 6 may be formed of a low viscosity epoxy resin, such as DER322 or DEH24. Naturally, various other materials to prevent attenuation of an ultrasonic signal may be used as one example of a constituent material of the lens layer 6. As a result of forming the lens layer 6 of a low-attenuation material, it may be possible to enhance the sensitivity of an ultrasonic signal.

Moreover, as a result of installing the lens layer 6 to cover a portion of the side surface of the acoustic module 8, i.e. a portion of the outer surface of the acoustic module 8, it may be possible to reduce crosstalk.

Hereinafter, the ultrasonic diagnostic instrument 1 including the acoustic module 8 and a controller 10 according to one embodiment will be described with reference to FIGS. 2 and 3.

Figure 2:
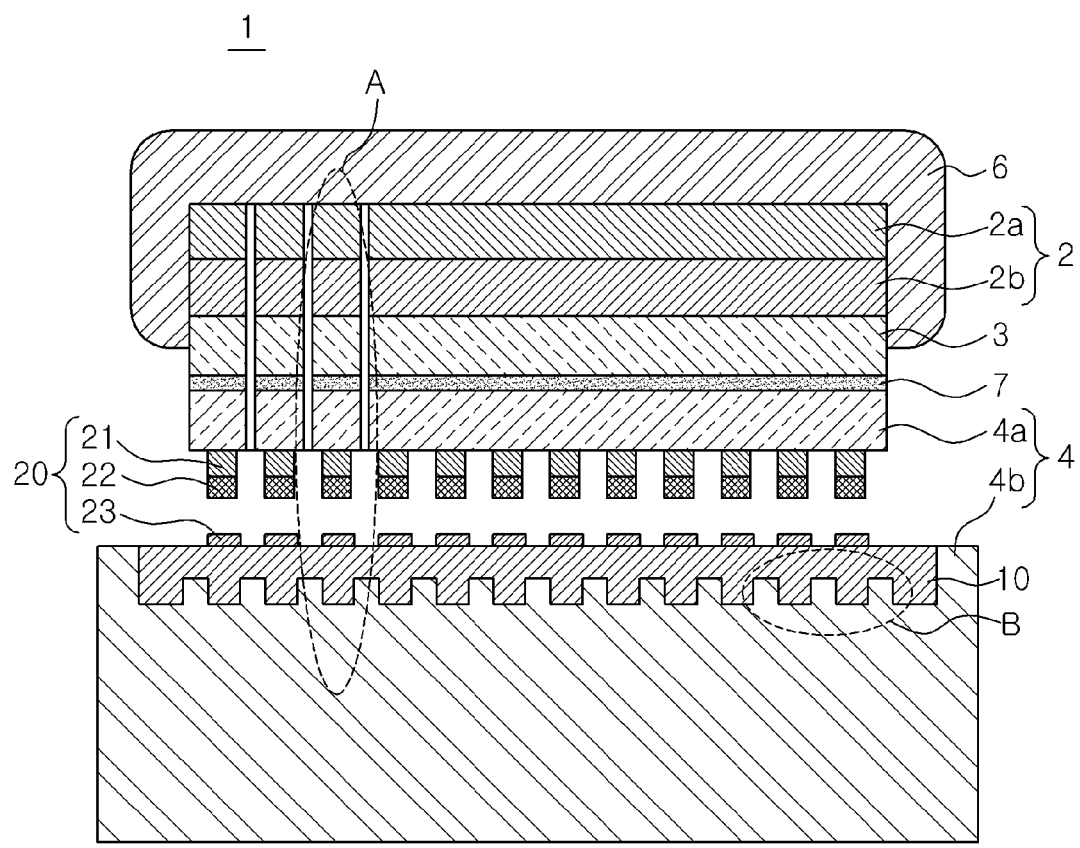
FIG. 2 is a sectional view of an ultrasonic diagnostic instrument before coupling of an acoustic module and a controller according to one embodiment.
Figure 3:
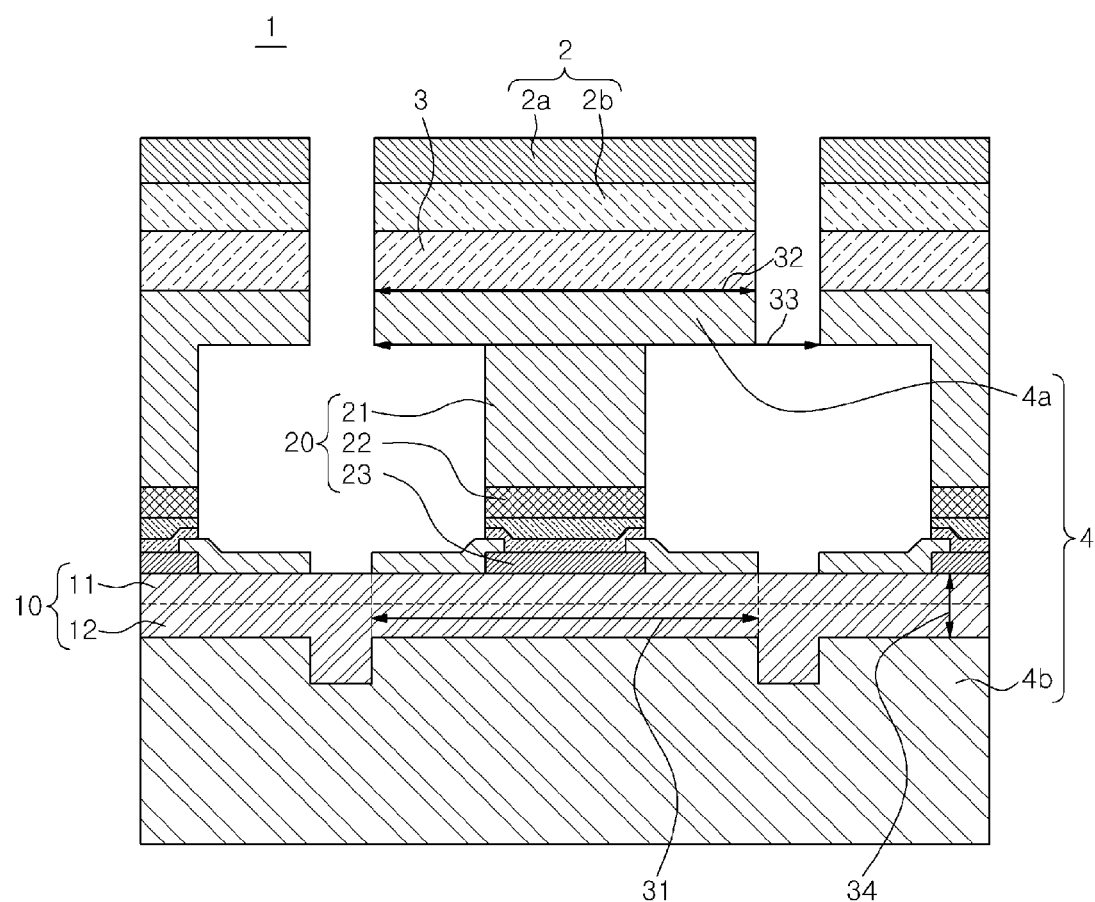
FIG. 3 is an enlarged sectional view of portion A of FIG. 2, showing the ultrasonic diagnostic instrument after coupling of the acoustic module and the controller according to the embodiment.

FIG. 2 is a sectional view of the ultrasonic diagnostic instrument 1 before coupling of the acoustic module 8 and a controller 10, and FIG. 3 is an enlarged sectional view of portion A of FIG. 2, showing the cross section of the ultrasonic diagnostic instrument 1 after coupling of the acoustic module 8 and the controller 10.

The ultrasonic diagnostic instrument 1 may include the lens layer 6, the matching layer 2, the transducer 3, a first acoustic absorption layer 4a, a first connector 7, the controller 10, a second connector 20, and a second acoustic absorption layer 4b.

The lens layer 6 may prevent attenuation of an ultrasonic signal generated in the transducer 3, thereby enhancing the sensitivity of the ultrasonic signal. The lens layer 6 may be installed to cover the matching layer 2, may be installed to cover the matching layer and the transducer 3, or may be installed to cover the matching layer, the transducer 3, and the first acoustic absorption layer 4a. Functions, materials, and the like of the lens layer 6 may be equal to or different from those of the lens layer 6 as mentioned above with reference to FIG. 1.

The matching layer 2 may reduce a difference in acoustic impedances between the transducer 3 and the subject to match the acoustic impedances of the transducer 3 and the subject with each other, thereby allowing ultrasonic waves generated in the transducer 3 to be efficiently transmitted to the subject.

In addition, the matching layer 2 may include a first matching layer 2a and a second matching layer 2b. More specifically, the matching layer 2 may be divided into the first matching layer 2a and the second matching layer 2b based on a region of the subject to be diagnosed, characteristics of the ultrasonic diagnostic instrument 1 including the transducer 3, and frequencies of ultrasonic waves to be transmitted or received. The first matching layer 2a and the second matching layer 2b may be formed of different materials to achieve different acoustic impedances, or may be formed of the same material. Functions, shapes, materials, and the like of the matching layer 2 may be equal to or different from those of the matching layer 2 as mentioned above with reference to FIG. 1.

The transducer 3 may convert an applied electrical signal into mechanical vibration to transmit ultrasonic waves, or may convert mechanical vibration into an electrical signal by receiving an ultrasonic signal reflected from a region to be diagnosed. Functions, shapes, materials, and the like of the transducer 3 may be equal to or different from those of the transducer 3 as mentioned above with reference to FIG. 1.

The first acoustic absorption layer 4a may be installed to the lower surface of the transducer 3 to absorb ultrasonic waves generated in and moving rearward of the transducer 3, thereby preventing ultrasonic waves from moving rearward of the transducer 3. In addition, the first acoustic absorption layer 4a may receive a control signal of the controller 10 through the second connector 20, and then transmit the control signal to the transducer 3 through the first connector 7, to enable generation of ultrasonic waves in the transducer 3.

To transmit a control signal of the controller 10 to the transducer 3, the first acoustic absorption layer 4a may be formed of a conductive material. For example, the first acoustic absorption layer 4a may be formed of tungsten (WC) having high impedance, thus amplifying a control signal of the controller 10 to transmit the amplified control signal to the transducer 3. Naturally, various other materials to transmit a control signal of the controller 10 to the transducer 3 may be used as one example of a constituent material of the first acoustic absorption layer 4a.

In addition, the impedance of the first acoustic absorption layer 4a may vary based on frequencies of ultrasonic waves to be transmitted or received and the structure of the first acoustic absorption layer 4a, but may have an approximate value of 100Ω.

The first connector 7 may be located between the transducer 3 and the first acoustic absorption layer 4a to physically and electrically connect the transducer 3 and the first acoustic absorption layer 4a to each other.

More specifically, the first connector 7 may physically couple the transducer 3 and the first acoustic absorption layer 4a to each other to transmit vibration of the transducer 3 to the first acoustic absorption layer 4a, which enables attenuation of vibration by the first acoustic absorption layer 4a. In addition, the first connector 7 may electrically couple the transducer 3 and the first acoustic absorption layer 4a to each other to transmit a control signal of the controller 10 to the transducer 3 for generation of ultrasonic waves and to transmit an electrical signal, converted from mechanical vibration by the transducer 3, to the controller 10.

In addition, although the first connector 7 may be formed of epoxy, naturally, various other materials to physically and electrically connect the transducer 3 and the first acoustic absorption layer 4a to each other may be used as one example of a constituent material of the first connector 7.

The controller 10 may be located between the second connector 20 and the second acoustic absorption layer 4b to transmit a control signal to the transducer 3 to enable generation of ultrasonic waves in the transducer 3, or to receive an electrical signal, converted from mechanical vibration, i.e. an ultrasonic signal reflected from a region to be diagnosed by the transducer 3.

More specifically, the controller 10 may independently process an external input signal or an electrical signal from the transducer 3, may convert a received signal, processed by an external system, into a control signal for generation of ultrasonic signals to transmit the control signal to the transducer 3, or may transmit an electrical signal, received from the transducer 3, to an external system.

In the case of independently processing an external input signal or an electrical signal of the transducer 3, the controller 10 may include a central processing unit and a graphics processing unit.

The central processing unit included in the controller 10 may be a microprocessor. The microprocessor is a processing unit in which an arithmetic logic unit, a register, a program counter, a command decoder, a control circuit, or the like is mounted on at least one silicon chip. The central processing unit may generate a control signal to control operation of the transducer 3, and transmit the generated control signal to the transducer 3 through the first acoustic absorption layer 4a. In addition, the central processing unit may receive an electrical signal converted by the transducer 3 and transmit the electrical signal to the graphics processing unit. According to embodiments, the central processing unit may generate a signal to control a switching element used to control each of plural transducers 3 in the form of an array, and transmit the generated control signal to the switching element.

The graphics processing unit is a processing unit that processes graphics information. The graphics processing unit may assist a graphics processing function of the central processing unit, or may implement graphics processing alone. The graphics processing unit may convert an ultrasonic signal received by the transducer 3 into an ultrasonic image signal, or may process a signal to display operation of the ultrasonic diagnostic instrument 1.

The controller 10 may include at least one switching element. The switching element may control the plural transducers 3 arranged in the form of a matrix array, a linear array, a convex array, or a concave array. The switching element may control one transducer 3, or two or more transducers 3.

The switching element may be formed of a semiconductor material to control the transducers 3. In this case, the semiconductor material may be silicon (Si), or compounds of silicon (Si), sapphire, germanium, quartz, and glass. Naturally, various other materials to control the transducers 3 may be used as one example of a semiconductor material.

Accordingly, when the central processing unit of the controller 10 applies an operational signal having a threshold voltage or more to the switching element, the switching element formed of a semiconductor material, as exemplarily shown in FIG. 3, may be divided into an active area 11 and an inactive area 12. Thereby, the controller 10 may transmit a control signal to the transducer 3 through the switching element.

A width W2; 31 of the switching element may be equal to or greater than a width W1; 32 of the corresponding transducer 3 controlled by the switching element (W1≤W2), and may be equal to or less than a pitch P; 33 of the transducer 3 (W2≤P). Here, the pitch P is the sum of the width of the transducer 3 controlled by the switching element and a gap between the corresponding transducer 3 and another transducer located at one side thereof. In addition, the width W2; 31 of the switching element may be equal to or greater than the width W1; 32 of the corresponding transducer 3 controlled by the switching element and be equal to or less than the pitch P; 33 of the transducer 3 (W1≤W2≤P).

In addition, a thickness H; 34 of the switching element may be a value acquired by dividing the wavelength of ultrasonic waves generated in the transducer 3 by an even number. For example, the thickness H; 34 of the switching element may be one of ½, ¼, ⅛, and ¹⁄₁₆ of the wavelength of generated ultrasonic waves (H=λ/2, λ/4, λ/8, or λ/16).

The controller 10 may have recesses formed in the lower surface thereof. The recesses may correspond to inserts of the second acoustic absorption layer 4b that will be described hereinafter. The recesses of the controller 10 may be formed by back-grinding, dicing, or etching.

More specifically, back-grinding is a process of removing an unnecessary film on a rear surface of a wafer and grinding an unnecessarily thick rear surface to reduce resistance and increase thermal conductivity. Dicing is a cutting process using a diamond blade on a high-speed rotating spindle. Etching is a process of removing an oxide film not coated with a photoresist film.

Naturally, various other methods may be used to form the recesses in the lower surface of the controller 10.

Shapes, and the like of the recesses will be described below in detail.

The second connector 20 may be located between the first acoustic absorption layer 4a and the controller 10 to electrically connect the first acoustic absorption layer 4a and the controller 10 to each other. The second connector 20 may include a pillar 21 formed of copper (Cu), a bump 22 formed of tin (Sn) and silver (Ag), and a pad 23 formed of gold (Au).

The second connector 20 may electrically connect the first acoustic absorption layer 4a and the controller 10 to each other by directly fusing the same to each other in a flip-chip manner using a lower electrode pattern, without an additional connection structure, such as a meal lead wire, or an intermediate medium, such as a ball grid array (BGA). More specifically, after the copper pillar 21 and the bump 22, attached to the first acoustic absorption layer 4a, are located above the pad 23 attached to the controller 10, pressure is applied to the first acoustic absorption layer 4a in a direction toward the controller 10 or heat is applied to the bump 22 until the bump 22 covers the pad 23 located at the upper surface of the controller 10. In this way, the second connector 20 may electrically connect the first acoustic absorption layer 4a and the controller 10 to each other.

The second acoustic absorption layer 4b may be installed to the lower surface of the controller 10 to absorb ultrasonic waves moving rearward of the transducer 3, not absorbed by the first acoustic absorption layer 4a. In addition, the second acoustic absorption layer 4b may prevent forward transfer of heat generated in the controller 10, thereby causing rearward transfer of heat.

The second acoustic absorption layer 4b may be formed of a thermally conductive material and an acoustic absorption material, and may have inserts.

More specifically, the thermally conductive material may include a Carbon Nano Tube (CNT) as a carbon allotrope, graphene, or graphite, or may include a composite of a carbon allotrope and a metal. The composite of the carbon allotrope and the metal may be produced by fusing each component, or may be produced by alternately stacking the carbon allotrope and the metal in respective layers. Naturally, various other materials to increase thermal conductivity may be used as one example of the thermally conductive material.

The acoustic absorption material may function to adjust acoustic impedance and attenuation constant. In a representative example, the acoustic absorption material may include epoxy. Naturally, various other materials to adjust acoustic impedance and attenuation constant may be used as one example of the acoustic absorption material. In addition, the acoustic absorption material may have different acoustic impedances per layer.

The second acoustic absorption layer 4b may be formed of at least one of the thermally conductive material and the acoustic absorption material, and may be formed by alternately arranging the thermally conductive material and the acoustic absorption material. Naturally, various other arrangements to adjust thermal conductivity, acoustic impedance, and attenuation constant of the second acoustic absorption layer 4b may be used as one example of the arrangement of the second acoustic absorption layer 4b.

The second acoustic absorption layer 4b may have the inserts formed at the upper surface thereof. The inserts have any one shape among cylindrical, semispherical, tetrahedral, pentagonal, and hexagonal shapes. Naturally, various other shapes to radiate heat generated in the controller 10 may be used as one example of the inserts of the second acoustic absorption layer 4b. The inserts of the second acoustic absorption layer 4b may be formed by back-grinding, dicing, or etching. Naturally, various other methods may be used as one example of a method of forming the inserts at the upper surface of the second acoustic absorption layer 4b.

Shapes, and the like of the inserts will be described below in detail.

The thermally conductive material of the second acoustic absorption layer 4b may have a square-wave shape, a cylindrical shape, or the like, and an empty space of the second acoustic absorption layer 4b may be filled with an acoustic absorption material to provide the ultrasonic diagnostic instrument 1 with appropriate acoustic impedance.

Accordingly, heat generated in the controller 10 may be transferred to the recesses formed in the lower surface of the controller 10, and then be transferred to the inserts formed at the upper surface of the second acoustic absorption layer 4b. The heat transferred to the inserts may be radiated while being propagated at the lower surface of the second acoustic absorption layer 4b through the thermally conductive material.

Hereinafter, a packaging coupling structure of the second acoustic absorption layer 4b having the inserts and the controller 10 having the recesses corresponding to the inserts according to different embodiments will be described with reference to FIGS. 4A to 6B.

Figure 4A:
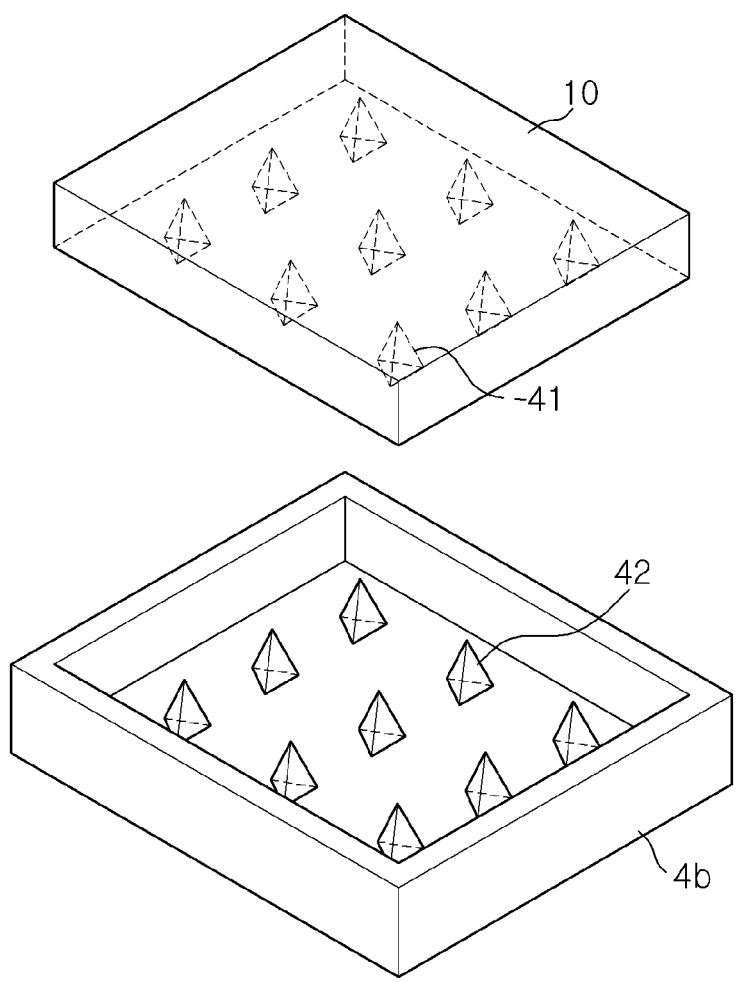
FIG. 4A is a perspective view showing an external appearance before coupling of a second acoustic absorption layer having tetrahedral inserts and a controller having recesses corresponding to the inserts according to one embodiment.
Figure 4B:
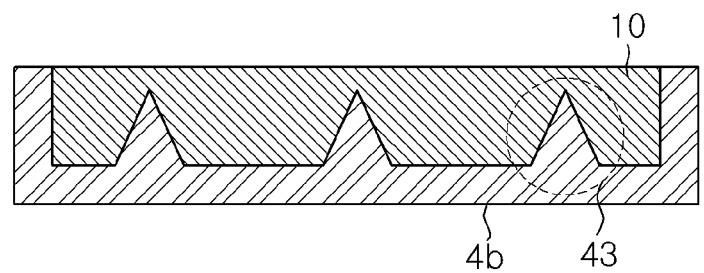
FIG. 4B is a sectional view showing a cross section after coupling of the second acoustic absorption layer having the tetrahedral inserts and the controller having the recesses corresponding to the inserts according to the embodiment of FIG. 4A.

FIG. 4A is an enlarged view of portion B of FIG. 2 and shows an external appearance before coupling of the second acoustic absorption layer 4b having tetrahedral inserts and the controller 10 having recesses corresponding to the inserts, and FIG. 4B is an enlarged view of portion B of FIG. 2 and shows a cross section after coupling of the second acoustic absorption layer 4b having the tetrahedral inserts and the controller 10 having the recesses corresponding to the inserts.

As exemplarily shown in FIG. 4A, the second acoustic absorption layer 4b may include tetrahedral inserts 42 and the controller 10 may include recesses 41 corresponding to the tetrahedral inserts 42. The tetrahedral inserts 42 and the recesses 41 corresponding to the inserts 42 may have the same size and the same direction to realize female-male engagement 43.

Thus, as exemplarily shown in FIG. 4B, when the second acoustic absorption layer 4b and the controller 10 are connected to each other, the inserts 42 and the recesses 41 may be packaged to coincide with each other in terms of size and direction, realizing the tetrahedral female-male engagement 43.

In this way, the controller 10 achieves an increased heat radiation area such that heat generated in the controller 10 may be transferred to the inserts 42 of the second acoustic absorption layer 4b through the recesses 41 of the controller 10 with high heat radiation efficiency. In addition, the second acoustic absorption layer 4b surrounds and packages the controller 10 to reduce damage to the controller 10, which may enhance durability of the ultrasonic diagnostic instrument 1.

Figure 5A:
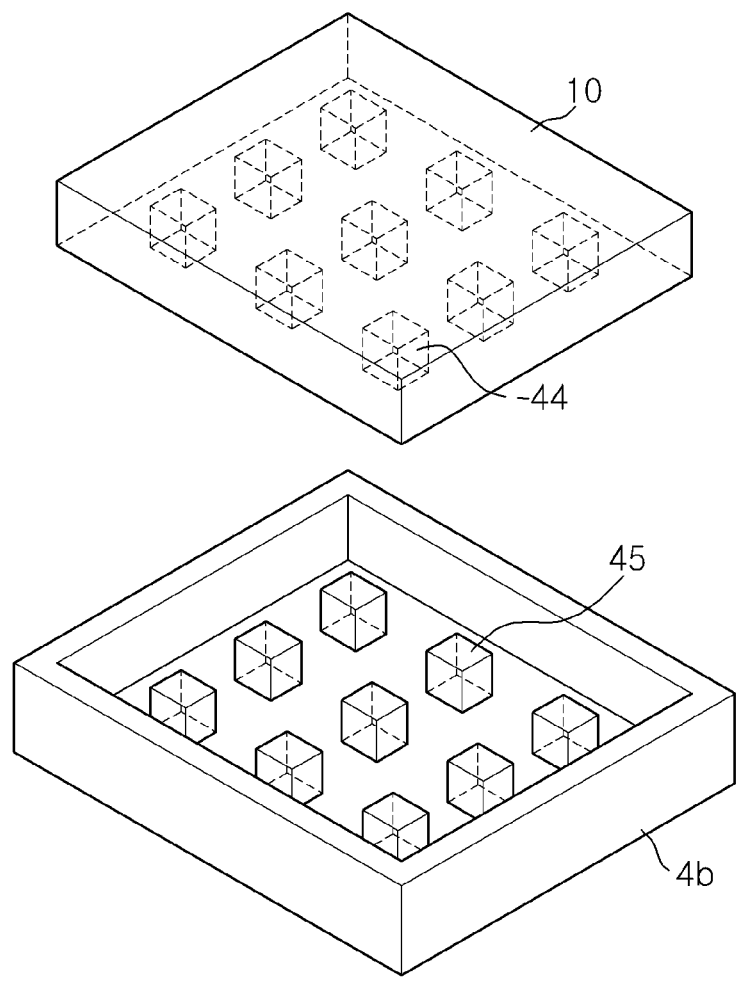
FIG. 5A is a perspective view showing an external appearance before coupling of a second acoustic absorption layer having hexahedral inserts and a controller having recesses corresponding to the inserts according to one embodiment.
Figure 5B:
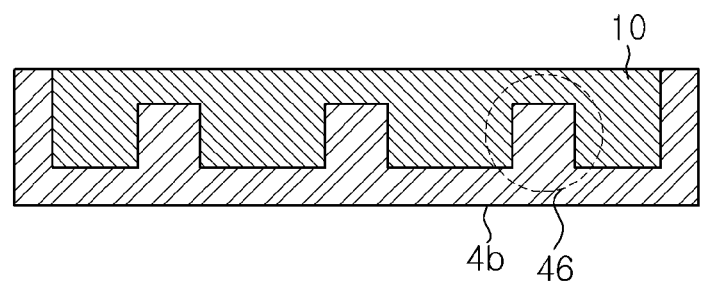
FIG. 5B is a sectional view showing a cross section after coupling of the second acoustic absorption layer having the hexahedral inserts and the controller having the recesses corresponding to the inserts according to the embodiment of FIG. 5A.

FIG. 5A is an enlarged view of portion B of FIG. 2 and shows an external appearance before coupling of the second acoustic absorption layer 4b having hexahedral inserts 45 and the controller 10 having recesses 44 corresponding to the inserts 45, and FIG. 5B is an enlarged view of portion B of FIG. 2 and shows a cross section after coupling of the second acoustic absorption layer 4b having the hexahedral inserts 45 and the controller 10 having the recesses 44 corresponding to the inserts 45.

As exemplarily shown in FIG. 5A, the second acoustic absorption layer 4b may include the hexahedral inserts 45 and the controller 10 may include recesses 44 corresponding to the hexahedral inserts 45. The hexahedral inserts 45 and the recesses 44 corresponding to the inserts 45 may have the same size and the same direction to realize female-male engagement 46.

Thus, as exemplarily shown in FIG. 5B, when the second acoustic absorption layer 4b and the controller 10 are connected to each other, the inserts 45 and the recesses 44 may be packaged to coincide with each other in terms of size and direction, realizing the hexahedral female-male engagement 46.

In this way, the controller 10 achieves an increased heat radiation area such that heat generated in the controller 10 may be transferred to the inserts 45 of the second acoustic absorption layer 4b through the recesses 44 of the controller 10 with high heat radiation efficiency. In addition, the second acoustic absorption layer 4b surrounds and packages the controller 10 to reduce damage to the controller 10, which may enhance durability of the ultrasonic diagnostic instrument 1.

Figure 6A:
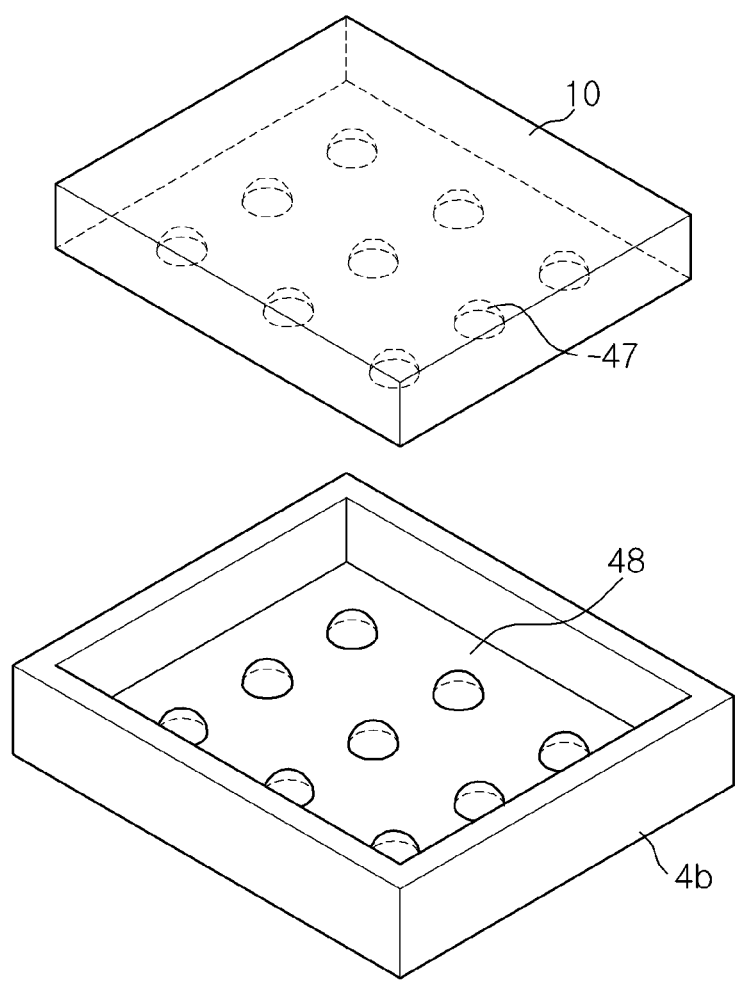
FIG. 6A is a perspective view showing an external appearance before coupling of a second acoustic absorption layer having semispherical inserts and a controller having recesses corresponding to the inserts according to one embodiment.
Figure 6B:
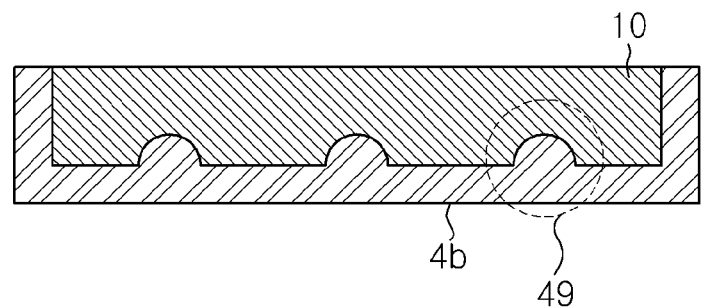
FIG. 6B is a sectional view showing a cross section after coupling of the second acoustic absorption layer having the semispherical inserts and the controller having the recesses corresponding to the inserts according to the embodiment of FIG. 6A.

FIG. 6A is an enlarged view of portion B of FIG. 2 and shows an external appearance before coupling of the second acoustic absorption layer 4b having semispherical inserts 48 and the controller 10 having recesses 47 corresponding to the inserts 48, and FIG. 6B is an enlarged view of portion B of FIG. 2 and shows a cross section after coupling of the second acoustic absorption layer 4b having the semispherical inserts 48 and the controller 10 having the recesses 47 corresponding to the inserts 48.

As exemplarily shown in FIG. 6A, the second acoustic absorption layer 4b may include the semispherical inserts 48 and the controller 10 may include the recesses 47 corresponding to the semispherical inserts 48. The semispherical inserts 48 and the recesses 47 corresponding to the inserts 48 may have the same size and the same direction to realize female-male engagement 49.

Thus, as exemplarily shown in FIG. 6B, when the second acoustic absorption layer 4b and the controller 10 are connected to each other, the inserts 48 and the recesses 47 may be packaged to coincide with each other in terms of size and direction, realizing the semispherical female-male engagement 49.

In this way, the controller 10 achieves an increased heat radiation area such that heat generated in the controller 10 may be transferred to the inserts 48 of the second acoustic absorption layer 4b through the recesses 47 of the controller 10 with high heat radiation efficiency. In addition, the second acoustic absorption layer 4b surrounds and packages the controller 10 to reduce damage to the controller 10, which may enhance durability of the ultrasonic diagnostic instrument 1.

Hereinafter, the transducers 3 in the form of a 2D matrix array according to one embodiment will be described with reference to FIG. 7.

Figure 7:
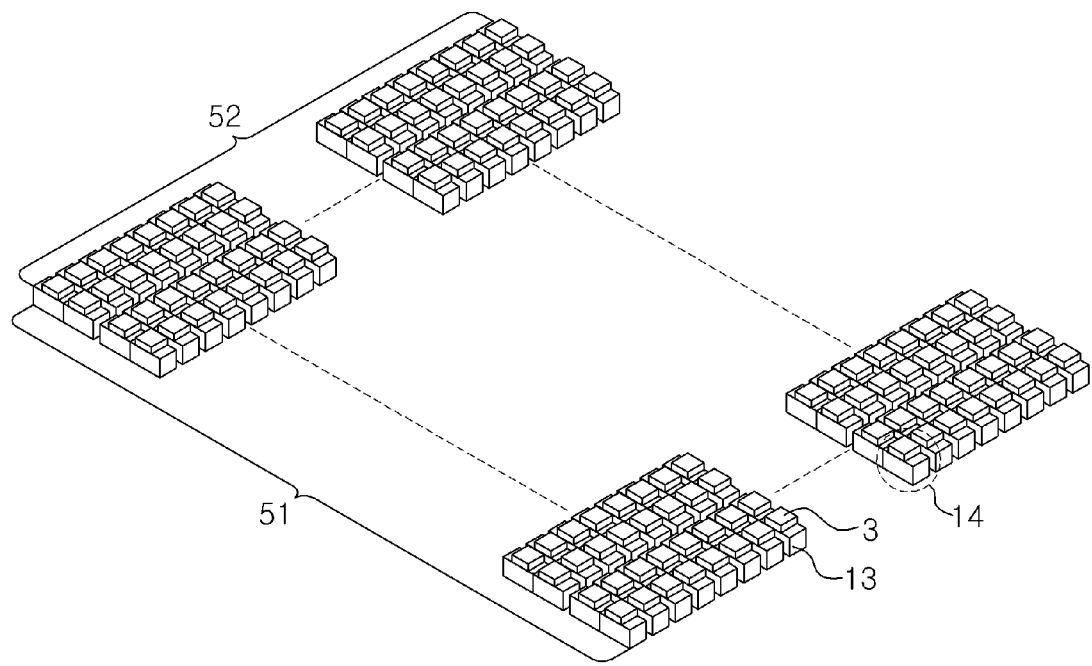
FIG. 7 is a perspective view showing an external appearance of an ultrasonic diagnostic instrument in which transducers are arranged in 2-dimensional matrix (144×72) according to one embodiment.

FIG. 7 shows an external appearance of the ultrasonic diagnostic instrument 1 in which the transducers 3 are arranged in a 2D matrix array (144×72).

A transducer module 14 may include one transducer 3 and one switching element 13 to control the transducer 3, and a plurality of transducer modules 14 may be arranged in a 2D matrix array as exemplarily shown in FIG. 7.

More specifically, 144 transducer modules 14 may be arranged in an abscissa 51 of the array and 72 transducer modules 14 may be arranged in an ordinate 52 of the array. Thus, the transducer modules 14 are arranged in a 2D matrix of 144×72, and a total of 10368 transducer modules 14 may be arranged.

However, the 2D matrix array is not limited to the matrix of 144×72, but is one example of the array of the transducer modules 14. The transducer modules 14 may take the form of a linear array, a convex array, or a concave array.

Hereinafter, a method of manufacturing the ultrasonic diagnostic instrument including the controller having the recesses and the second acoustic absorption layer having the inserts according to one embodiment will be described with reference to FIG. 8.

Figure 8:
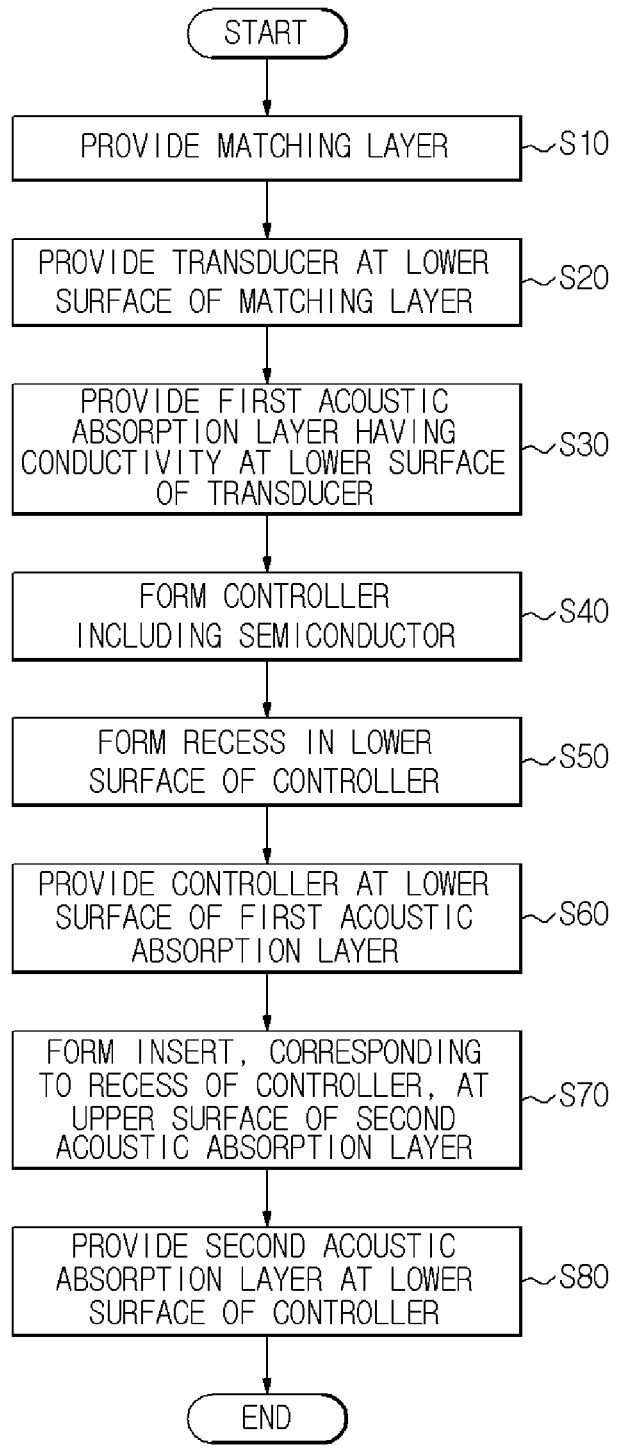
FIG. 8 is a flowchart of a method of manufacturing an ultrasonic diagnostic instrument according to one embodiment.

FIG. 8 is a flowchart of a method of manufacturing the ultrasonic diagnostic instrument.

A matching layer may first be provided (S10), and a transducer to transmit and receive ultrasonic waves may be provided at a lower surface of the matching layer (S20). Then, after providing a first acoustic absorption layer having conductivity at a lower surface of the transducer (S30), a controller including a semiconductor switching element may be formed (S40), and recesses may be formed in a lower surface of the controller by back-grinding, dicing, etching, or the like (S50).

The controller may be provided at a lower surface of the first acoustic absorption layer (S60). Then, inserts corresponding to the recesses of the controller may be formed at an upper surface of the second acoustic absorption layer by back-grinding, dicing, etching, or the like (S70). Finally, as the second acoustic absorption layer is provided at the lower surface of the controller (S80), the ultrasonic diagnostic instrument may be manufactured.

As is apparent from the above description, according to an ultrasonic diagnostic instrument and a method of manufacturing the ultrasonic diagnostic instrument, it may be possible to enhance radiation efficiency of heat generated in a transducer and to increase durability of the ultrasonic diagnostic instrument.

It will be apparent that the above description merely exemplifies the technical spirit, and various modifications, variations, and substitutions may be made by those skilled in the field of medical appliances without departing from the fundamental characteristics of the disclosure. Thus, it should be understood that there is no intent to limit the technical spirit to the disclosed embodiments and the accompanying drawings. Rather, the disclosed embodiments and the accompanying drawings are provided to explain the technical spirit, and the scope of the disclosure should be defined by the following claims, and all equivalent technical ideas should be construed as falling within the spirit and scope as defined by the claims.

What is claimed is:

1. An ultrasonic diagnostic instrument comprising:
a matching layer;
at least one transducer provided at a lower surface of the matching layer to generate ultrasonic waves;
a first acoustic absorption layer provided at a lower surface of the transducer to transmit an ultrasonic wave generation signal to the transducer;
a controller provided at a lower surface of the first acoustic absorption layer to control operation of the transducer, the controller having a recess formed in a lower surface thereof; and
a second acoustic absorption layer provided at the lower surface of the controller and having an insert formed at an upper surface thereof, the insert corresponding to the recess of the controller,
wherein the at least one transducer includes a plurality of transducers in the form of a matrix array, a linear array, a convex array, or a concave array,
wherein the controller includes a plurality of switching elements to control the respective transducers, and the switching elements take the form of a matrix array, a linear array, a convex array, or a concave array, and
wherein a width of each switching element is equal to or greater than a width of a corresponding one of the transducers controlled by the switching element.

2. The instrument according to claim 1, wherein the first acoustic absorption layer includes a conductive material.

3. The instrument according to claim 1, wherein the second acoustic absorption layer includes a carbon allotrope.

4. The instrument according to claim 1, wherein the second acoustic absorption layer includes a composite of a carbon allotrope and a metal.

5. The instrument according to claim 1, wherein the second acoustic absorption layer includes a thermally conductive material and an acoustic absorption material alternately arranged.

6. The instrument according to claim 1, wherein the insert has one shape among cylindrical, semispherical, tetrahedral, pentagonal, and hexahedral shapes.

7. The instrument according to claim 1, wherein the width of each switching element is equal to or less than the sum of the width of the corresponding one of the transducers controlled by the switching element and a gap between the corresponding transducer and another transducer located at one side thereof.

8. The instrument according to claim 1, wherein a thickness of each switching element has a value acquired by dividing the wavelength of ultrasonic waves generated by the corresponding one of the transducers controlled by the switching element by an even number.

9. A method of manufacturing an ultrasonic diagnostic instrument, the method comprising:
providing a matching layer;
providing at least one transducer at a lower surface of the matching layer;
providing a first acoustic absorption layer at a lower surface of the transducer;
forming a recess in a lower surface of a controller;
providing the controller at a lower surface of the first acoustic absorption layer;
forming an insert at an upper surface of a second acoustic absorption layer, the insert corresponding to the recess of the controller;
providing the second acoustic absorption layer at the lower surface of the controller; and
arranging a plurality of transducers in the form of a matrix array, a linear array, a convex array, or a concave array; and
forming the controller such that the controller includes a plurality of switching elements to control the respective transducers,
wherein a width of each switching element is equal to or greater than a width of a corresponding one of the transducers controlled by the switching element.

10. The method according to claim 9, further comprising forming the first acoustic absorption layer using a conductive material.

11. The method according to claim 9, further comprising forming the second acoustic absorption layer using a carbon allotrope.

12. The method according to claim 9, further comprising forming the second acoustic absorption layer using a composite of a carbon allotrope and a metal.

13. The method according to claim 9, further comprising forming the second acoustic absorption layer by alternately arranging a thermally conductive material and an acoustic absorption material.

14. The method according to claim 9, wherein the insert formed at the upper surface of the second acoustic absorption layer has one shape among cylindrical, semispherical, tetrahedral, pentagonal, and hexahedral shapes.

15. The method according to claim 9, wherein the width of each switching element is equal to or less than the sum of the width of the corresponding one of the transducers controlled by the switching element and a gap between the corresponding transducer and another transducer located at one side thereof.

16. The method according to claim 9, wherein a thickness of each switching element has a value acquired by dividing the wavelength of ultrasonic waves generated by the corresponding one of the transducers controlled by the switching element by an even number.

* * * * *